(12) United States Patent
Citron et al.

(10) Patent No.: US 7,134,969 B2
(45) Date of Patent: Nov. 14, 2006

(54) GOLF POSTURE BRACE AND GARMENT

(76) Inventors: Lowell A. Citron, 21 Bounty La., Jericho, NY (US) 11753; Michael A. Feinberg, 80 Plymouth Rd., Plainview, NY (US) 11803

(*) Notice: Subject to any disclaimer, the term of this patent is extended or adjusted under 35 U.S.C. 154(b) by 100 days.

(21) Appl. No.: 10/809,522

(22) Filed: Mar. 26, 2004

(65) Prior Publication Data

US 2004/0235581 A1 Nov. 25, 2004

Related U.S. Application Data

(60) Provisional application No. 60/458,947, filed on Apr. 1, 2003.

(51) Int. Cl.
*A63B 69/36* (2006.01)
*A61F 5/00* (2006.01)

(52) U.S. Cl. .............. 473/277; 473/464; 602/5
(58) Field of Classification Search ........... 473/207, 473/215, 227, 276, 464, 277; 602/5, 4, 19, 602/20, 50, 61, 62; 482/148; 2/44, 455
See application file for complete search history.

(56) References Cited

U.S. PATENT DOCUMENTS

| | | | |
|---|---|---|---|
| 756,237 A | 4/1904 | Hunkins | |
| 1,849,628 A * | 3/1932 | Lemercier | 244/143 |
| 3,697,065 A | 10/1972 | Glassburner et al. | |
| 3,820,794 A * | 6/1974 | Inoue | 473/215 |
| 3,901,579 A | 8/1975 | Demerest | |
| 4,121,688 A * | 10/1978 | Lirakis | 182/3 |
| 4,177,877 A * | 12/1979 | Gallinati | 182/3 |
| 4,318,546 A | 3/1982 | Chen | |
| 4,422,643 A | 12/1983 | Cushing | |
| 4,582,325 A * | 4/1986 | Yuhara | 473/215 |
| 4,731,882 A * | 3/1988 | Ekman | 2/69 |
| 4,758,000 A | 7/1988 | Cox | |
| 4,890,841 A | 1/1990 | Brooks | |
| 5,050,885 A | 9/1991 | Ballard et al. | |
| 5,435,563 A | 7/1995 | Salvatore | |
| 5,441,271 A | 8/1995 | Briggs | |
| 5,451,060 A | 9/1995 | Dalbo | |
| 5,460,385 A * | 10/1995 | Lazzeroni | 473/464 |
| 5,586,761 A | 12/1996 | Brock et al. | |
| 5,613,926 A * | 3/1997 | Michaelson | 482/121 |
| 5,658,203 A | 8/1997 | Shub | |
| 5,785,603 A * | 7/1998 | Lazier | 473/215 |
| 5,795,238 A | 8/1998 | Nicholson | |
| 5,857,990 A | 1/1999 | Maas | |
| 5,937,442 A * | 8/1999 | Yamaguchi et al. | 2/69 |
| 6,101,631 A * | 8/2000 | Ferguson, Jr. | 2/94 |
| 6,174,270 B1 | 1/2001 | Dagenais | |
| 6,371,863 B1 | 4/2002 | Moran | |
| 6,378,465 B1 * | 4/2002 | Austin | 119/770 |
| 6,440,094 B1 | 8/2002 | Maas | |
| 6,612,845 B1 * | 9/2003 | Macri et al. | 434/247 |
| 6,626,131 B1 * | 9/2003 | Moulton, III | 119/770 |

OTHER PUBLICATIONS http://www.teamresultz.com "Saunders Posture S'port".
http://www.thesaundersgroup.com "Posture Corrector".

* cited by examiner

*Primary Examiner*—Nini F. Legesse
(74) *Attorney, Agent, or Firm*—Kenyon & Kenyon LLP

(57) ABSTRACT

A device and method are provided for encouraging or ensuring proper posture of a golfer during a golf swing. In certain embodiments, the device may be in the form of a brace comprising a strap that fits around the body to resist or prevent excessive bending of the spine, or "hunching over," during the golf swing. The brace may have a single, continuous strap that winds around the body, forming a crossing pattern across the spine and passing over both shoulders, with the ends of the strap meeting in the front of the body. The ends of the strap may be suitably joined, for example by a buckle, to allow adjustment. The brace may be an integral part of a garment, which may have an outer shell and inner lining.

16 Claims, 5 Drawing Sheets

OUTSIDE SHELL

OUTSIDE SHELL

PLACEMENT OF STRAPS

PLACEMENT OF STRAPS

GOLF POSTURE BRACE AND GARMENT

CROSS-REFERENCE TO RELATED APPLICATIONS

This application claims priority to U.S. Provisional Patent Application Ser. No. 60/458,947, filed Apr. 1, 2003, entitled "Golf Posture Brace and Garment," the disclosure of which is hereby incorporated herein by reference.

FIELD OF THE INVENTION

The invention relates to the fields of golf training equipment and orthopedic supports and/or garments.

BACKGROUND OF THE INVENTION

While the importance of strength, flexibility, and conditioning has been a primary focus in enhancing athleticism and performance, the role of posture has been comparatively ignored. However, without proper posture, dynamic and coordinated movement will never be optimized. This is because the skeletal system serves as the framework on which muscles act. Sub-par skeletal alignment will result in decreased performance.

While posture is important to many sports, in the game of golf it plays one of the most important, if not the most important role. This concept was very simply stated by Ben Hogan by which he stated, "The proper stance and posture enable a golfer to be perfectly balanced and poised throughout the golf swing. Only then will his legs, arms, and body be able to carry out their interrelated assignments correctly."

One of the most common errors in golf poster is a "hunching over" of the spine or rounding of the shoulders during the golf swing. This results from excessive bending of the thoracic vertebrae and leads to poor mechanics and performance and possible injury.

A specific example of incorrect golf posture is seen when evaluating the biomechanical effects of one of the most common swing faults of amateur golfers, the "reverse-C" position. A "reverse-C" results when a golfer laterally slides the hips forward during downswing while the head lags behind and weight remains on the trailing side (typically, the right side). This motion results in a "C" position of the spine at finish, which creates 50%–80% more force than a properly executed golf swing which results in a neutral spine. (The Physician and Sports Medicine, Vol.27, NO.7, July 1999.) In fact myoelectric studies of lumbar spine muscles (L3–L4) show greater activity in amateurs than professionals. Data indicates that amateurs generate 80% greater lateral bending and shear forces and 50% more torque. These may predispose golfers with incorrect posture to muscle strains, facet injuries and herniated discs.

SUMMARY OF THE INVENTION

In certain embodiments, the invention is directed to providing a device a method for encouraging or ensuring proper posture of a golfer during a golf swing.

In certain embodiments, the device may be in the form of a brace comprising a strap that fits around the body to resist or prevent excessive bending of the spine, or "hunching over," during the golf swing.

In an embodiment illustrated in the accompanying drawings and described below, the brace has a single, continuous strap that winds around the body, forming a crossing pattern across the spine and passing over both shoulders, with the ends of the strap meeting in the front of the body. In that illustrated embodiment, the ends of the strap are suitably joined, for example by a buckle. This allows the wearer to individually adjust the brace's fit and tension through a simple process, by just adjusting the strap at the area where the ends are joined, for example by loosening or tightening the strap at the buckle. The use of a single strap results in the application of equal force throughout the anterior strap portions of the brace as the brace pulls the shoulders back and helps the wearer achieve optimal posture.

In certain embodiments, a suitable brace may be incorporated with a base garment. The base garment may be a lightweight jacket and/or shirt and/or vest. In an embodiment illustrated in the accompanying drawings and described below, the garment itself is comprised of an outer shell with an inner lining. These two garment portions may be suitably joined. The inner lining may be constructed with tunnels and/or loops for the brace. The anterior of the outer shell may have openings for allowing access to the area between the outer shell and inner lining to adjust the brace.

In a method of encouraging or ensuring proper posture during a golf swing, a golfer wears the brace and/or garment with the brace, adjusts the brace to provide proper tension, and leaves the tensioned brace in place while engaging in the golf swing. After the golfing activity is completed, the brace and/or garment with the brace is removed.

DETAILED DESCRIPTION

The following is a description of the brace and garment illustrated in the Figures. It should be understood that the invention is not limited to the embodiment illustrated as an example, and is capable of variation within the scope of the claims.

Figure 1:
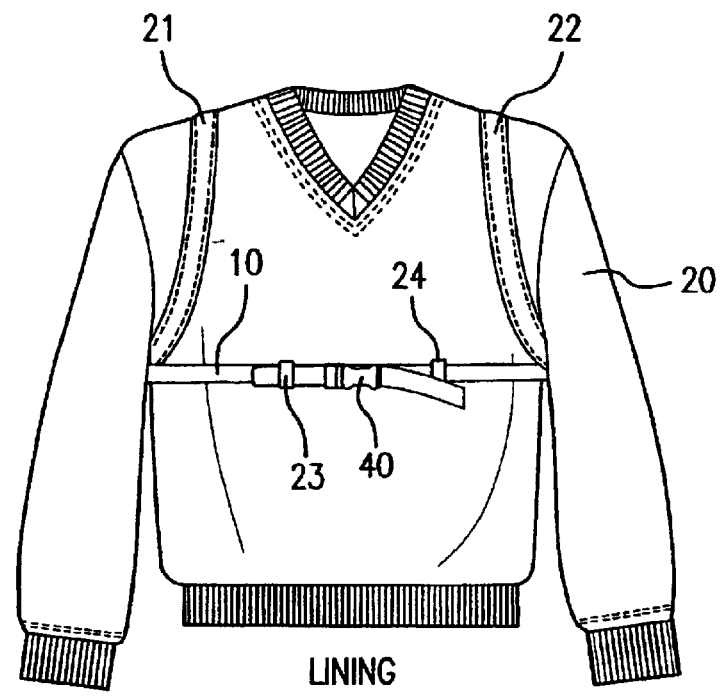
FIG. 1 is a front view of an inner lining and brace in accordance with one possible embodiment of the invention.
Figure 2:
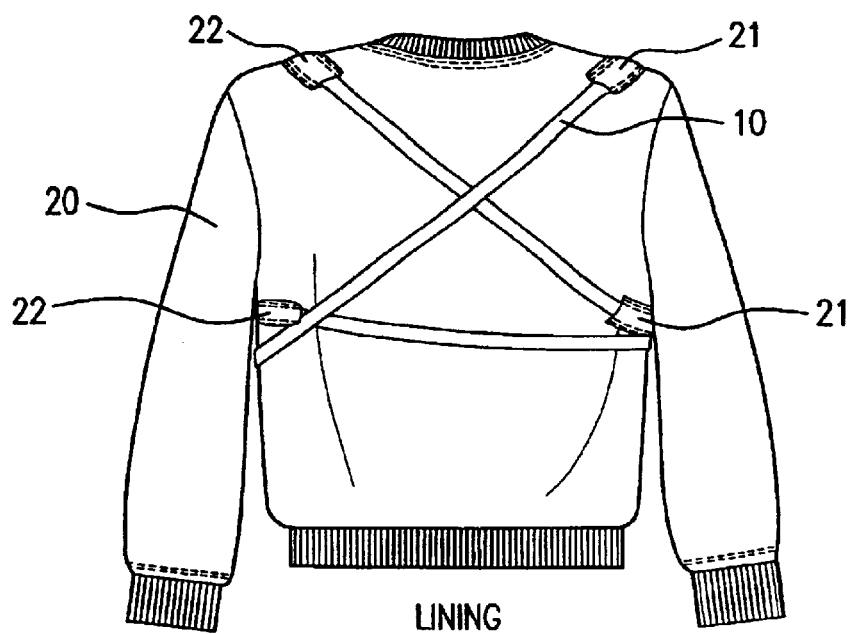
FIG. 2 is a rear view of the inner lining and brace shown in FIG. 1.

In the example illustrated, the base garment may be a lightweight wind jacket and/or wind shirt and/or vest comprising an outer shell 30 (FIGS. 3–4) and an inner lining 20 (FIGS. 1–2). The outer shell 30 and inner lining 20 may be manufactured from any suitable materials. For example, the outside shell may be manufactured from a woven fabric made from 100% polyester with a peached finish. The inner lining, for example, may be a knit jersey lining made from 65% polyester/35% cotton. These materials for the outside shell and inner lining are considered appropriate for a number of reasons, for example, cosmetic appearance, durability, and comfort. Many other materials are possible.

In the example illustrated, the garment is collarless with a ribbed V-shaped neck-line, for example ribbed with cotton trim. The illustrated waistband and sleeve cuffs are also ribbed trimmed. Alternatively, the garment can be manufactured with a rounded, crew neck or rounded neck with two or three button or snap closures. Many other possible variations of the style and look of the garment are possible.

FIGS. 1 and 2 show the inner lining 20 along with the brace 10. The inner lining 20 serves to help encase the brace 10. This helps to keep the brace 10 in the desired position.

The illustrated brace 10 comprises a strap and a mechanism for joining the strap ends, such as buckle 40. This makes the strap freely adjustable.

The inner lining 20 and outer shell 30 may be, if desired, joined together in any of a number of suitable manners. If the inner lining 20 and outer shell 30 are joined, they should preferably be joined in such a way as not to inhibit the operation of the brace 10.

The inner lining 20 may have one or more integral tunnels 21, 22 and/or loops 23, 24, through which the strap portions of the brace 10 pass. In the illustrated embodiment, the tunnels 21, 22 are designed to pass under the axilla (armpit) and over the clavicle (collar bone). The tunnels 21, 22 provide direction for the straps and comfort to a sensitive region of the anatomy. The tunnels may be padded, as described below. The construction of the tunnels in the illustrated embodiment does not add excessive bulk to the garment or create any significant resistance to the movement of the straps. Other constructions and placements of tunnels and/or loops are possible within the scope of the invention.

Figure 3:
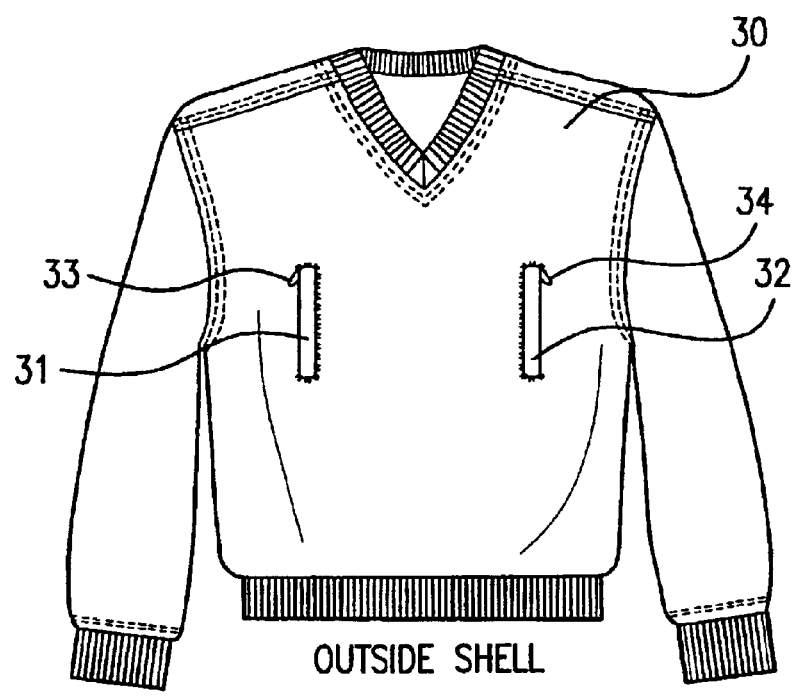
FIG. 3 is a front view of an outer shell to accompany the inner lining and brace of the embodiment shown in FIG. 1.
Figure 4:
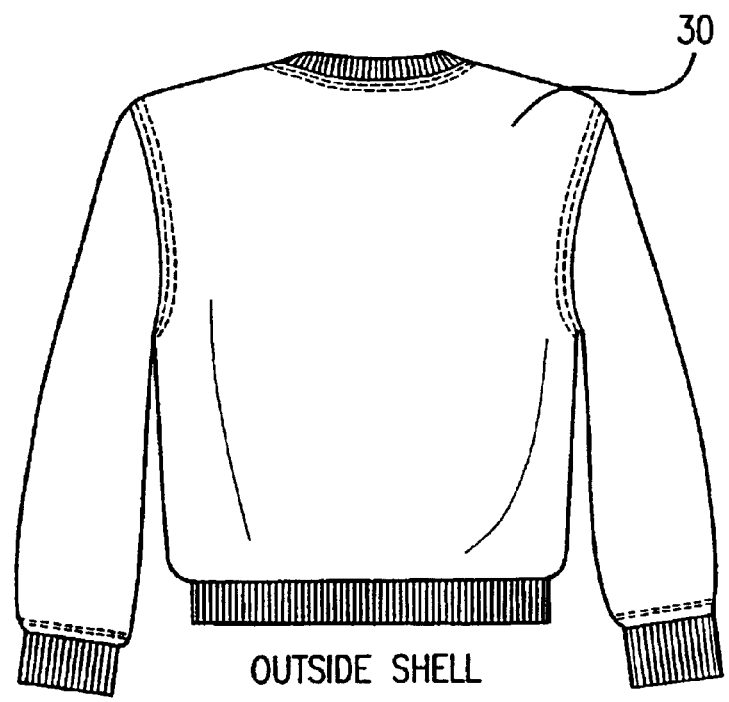
FIG. 4 is a rear view of the outer shell shown in FIG. 3.

FIGS. 3 and 4 show the outer shell 30. In the illustrated embodiment, the anterior of the garment has two 8" length openings 31, 32, which may be opened and closed by zippers 33, 34, running vertically on the front. The tops of the zippers are located 9" from the high point shoulder ("HPS") of the garment and are 10" apart. These zippered openings 31, 32 allow convenient access to the area between the inner lining 20 and the outer shell 30 where the self-contained brace 10 is located. The zippered openings 31, 32 thus provide access to the two end straps of the brace 10 and the fastening buckle 40, allowing for convenient adjustment of the brace 10. Other constructions of the openings 31, 32, including variations in size, shape, location, number, and manner of closing, are possible.

Figure 5:
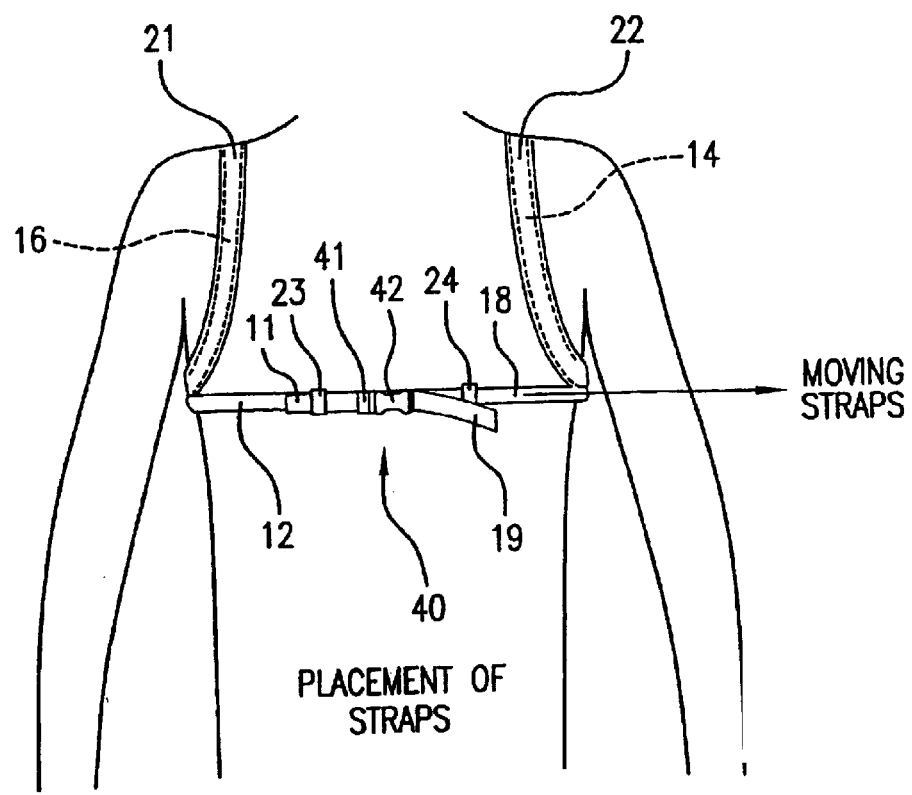
FIG. 5 is a front view showing the strap placement of the brace of FIG. 1.
Figure 6:
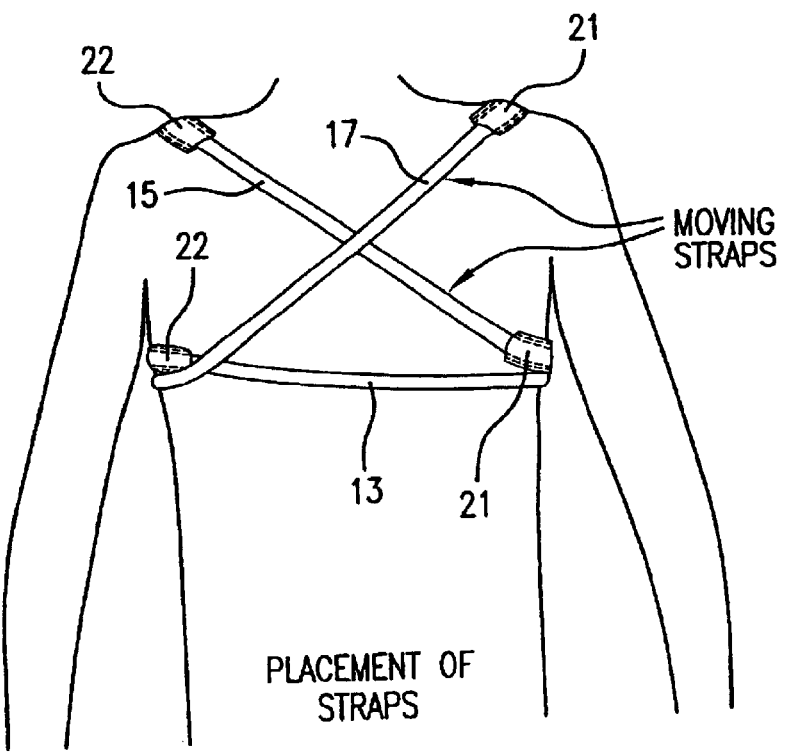
FIG. 6 is a rear view showing the strap placement of the brace of FIG. 1.
Figure 7:
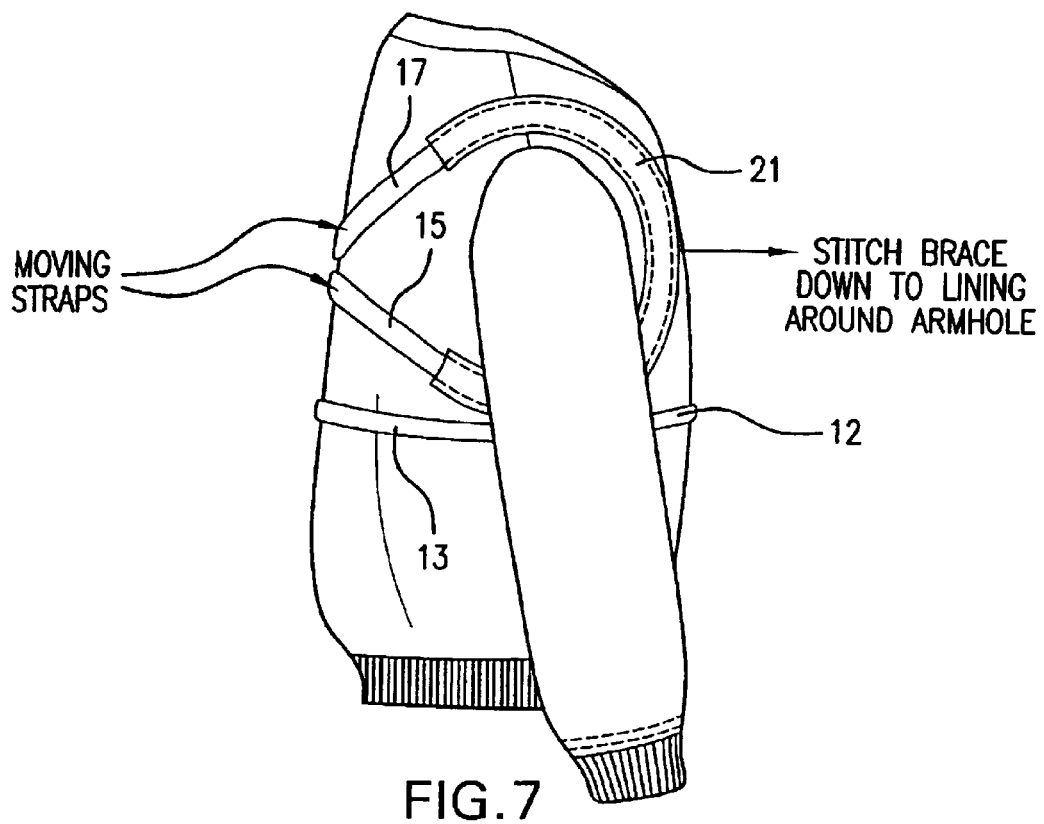
FIG. 7 is a side view showing the strap placement of the brace of FIG. 1.

FIGS. 5 through 7 illustrate where the strap portions of the brace 10 lie from an anatomical standpoint, as seen through the garment. Starting from a right strap end 11, the strap includes a right front strap portion 12 that passes through a right buckle part 41. The right front strap portion 12 passes through loop 23 and around the right front side of the wearer.

The right front strap portion 12 continues to a crossing back strap portion 13, visible in FIG. 6. As crossing back strap portion 13 approaches the left side, the strap passes into tunnel 22. The strap then continues as left shoulder strap portion 14, through the tunnel 22 and over the left shoulder.

As shown in FIG. 6, the strap exits the tunnel 22 at the top of the left shoulder and continues as first diagonal strap portion 15. Under the right armpit, the strap then enters tunnel 21. The strap then continues as right shoulder strap portion 16, through the tunnel 21 and over the right shoulder.

As shown in FIG. 6, the strap exits the tunnel 21 at the top of the right shoulder and continues as second diagonal strap portion 17. Under the left armpit, the second diagonal strap portion 17 continues around to the front of the wearer as left front strap portion 18. The left front strap portion 18 passes through loop 24 and left buckle part 42. The left front strap portion then terminates at left strap end 19.

The tension in the brace 10 is adjustable by adjusting the strap in relation to the buckle 40. For example, the right front strap portion 12 may be adjusted within right buckle part 41, and/or the left front strap portion 18 may be adjusted within left buckle part 42. The left strap end 11 and/or the right strap end 19 may be tucked under the respective loop 23, 24.

Some dimensions of some of the features of the illustrated embodiment are as follows, although many variations are of course possible. The brace strap may be, for example, 1½" in width. It may be designed to cross the anterior of the garment about 8½" down from the high point shoulder (HPS). The strap loops 23, 24 may be 2" in length and ¾" wide and sewn into the garment. The strap tunnels that run through the armpit may end on the posterior aspect of the garment at a distance 2" over the HPS.

Figure 8:
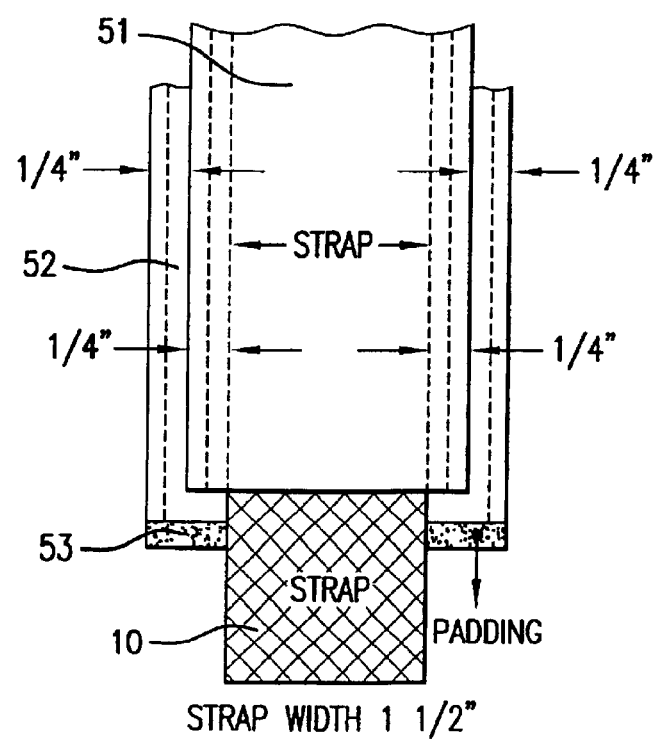
FIG. 8 shows a top view of an example of a strap tunnel construction.
Figure 9:
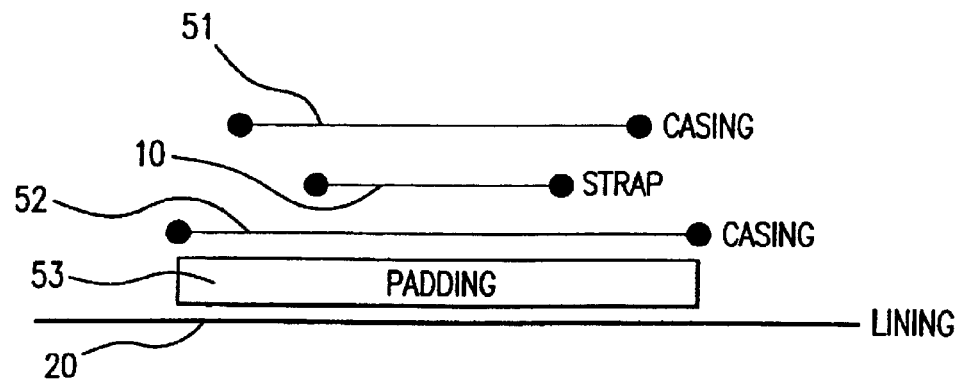
FIG. 9 shows a schematic cross-sectional view of the strap tunnel construction of FIG. 8.
Figure 10:
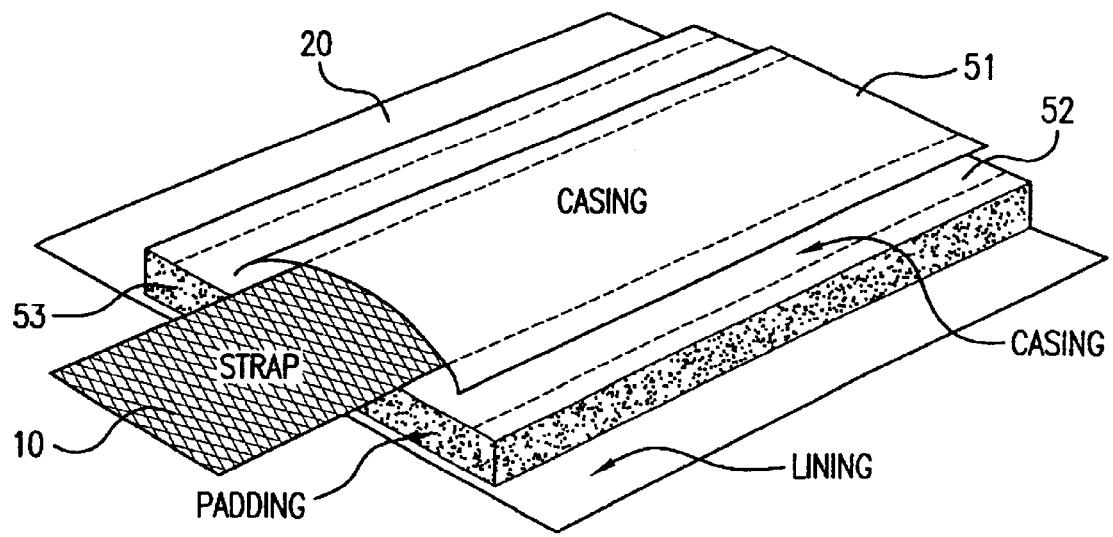
FIG. 10 shows a perspective view of the strap tunnel construction of FIG. 8.

FIGS. 8 through 10 illustrate an example of a tunnel construction. Attached to the lining 20 is an outer tunnel casing 51 and an inner tunnel casing 52. A layer of padding 53 may be provided under the inner tunnel casing 52. The strap of the brace 10 passes between the inner tunnel casing 52 and the outer tunnel casing 51. For a strap width of 1½", the casing and padding may be selected to have widths of 2" and 2½" respectively. These dimensions allow for uninhibited movement of the strap portions and provide comfort. Various alternatives of the tunnel construction are possible. For example, the inner tunnel casing and/or padding may be omitted, and the dimensions may of course be changed.

As can be appreciated from the illustrations and description, the garment is designed and engineered to provide comfort and function, while at the same time serving the purpose of the brace design, which is to dynamically enhance and promote proper posture, specifically thoracic spine posture. The action of the brace serves to resist or prevent excessive bending of the spine, or "hunching over," during the golf swing.

The golf posture brace promotes proper thoracic spine posture, while allowing the golfer the ability to freely swing the club. With the specific inventive aspects discussed, the golf posture brace is a golf training aide designed for function. It can be utilized as a static training aide to providing muscle reeducation and biofeedback or as a dynamic swing aide. It is a training aide that can be inconspicuously utilized on the practice tee, lesson tee and the course.

Proper posture in golf, or what a golf teaching professional might call "spine angle," is the angle formed by the player's spine and club shaft at address. Address posture is the static stance just prior to initiating movement of the club away from the ball. It has been widely accepted that this angle should be about ninety degrees. The most important position and anatomical consideration of address posture is a proper thoracic curve. While this is the most important, it is also most abused. In a study of golf professionals it was determined that more than ninety percent of golfers are unable to achieve proper posture, and as a result golfers are unable to perform a proper swing. A swing that allows for a high level of performance also limits injury.

Once proper posture is achieved the next most important aspect of the golf swing is the ability for a golfer to maximize "shoulder turn," a golf term. A golfer's turn is his ability to rotate his thoracic spine, and spinal rotation is most available in the upper thoracic spine, $T_1$–$T_6$. Therefore, limited thoracic rotation will limit a golfer's ability to perform. Specifically, an excessive thoracic kyphosis (hunchback) will limit thoracic rotation or "shoulder turn," as a result of the change in facet orientation. Simply put, poor thoracic spine posture will cause the spine in essence to lock up. A brace in accordance with the invention helps promote good thoracic spine posture and helps avoid the adverse effects of poor thoracic spine posture. The tension created by the first diagonal strap portion 15 and the second diagonal strap portion 17 across the spine help resist excessive bending of the spine. Similarly, the tension in the left shoulder strap portion 14 and the right shoulder strap portion 16 may help keep the shoulders back.

It will be appreciated that a brace in accordance with the invention may also be useful in the treatment and/or prevention of injury, specifically, injuries, pathologies and musculoskeletal derangements of, but not limited to the neck, shoulder and thoracic spine. Some of the more common injuries in these areas are a) tendonitis, b) impingement syndromes, and c) winging scapula. Through a comprehensive program consisting of dynamic stabilization, along with a therapeutic stretching and exercise program, many of these musculoskeletal disorders can be resolved, and more importantly prevented.

The treatment and prevention of injury through dynamic bracing is accomplished by helping the patient/wearer achieve optimal posture by utilizing an external bracing system. By promoting proper posture, many different results and derived benefits are obtained. Some of these benefits are as follows:

1. Promoting proper positioning of the scapula on the posterior thorax (scapulothoracic) articulation allows for more coordinated movement, e.g., increased scapulo-thoracic and gleno-humeral rhythm.
2. Promoting proper positioning and movement of the scapula and proper and coordinated movement of the shoulder joint helps prevent the development of impingement syndromes and tendonitis, such as those of the rotator cuff, supra- and infra-spinatus tendon.
3. Promoting a normal thoracic kyphosis (posterior convexity of spine) helps prevent a compensatory increase in the lumbar lordosis (posterior concavity of spine) and associated problems, such as an anterior tilting of the pelvis and hamstring tightness, which can lead to lower back problems.
4. Preventing forward head posture helps avoid a tightening of the deep cervical musculature, which can result in neck pain and/or migraine/tension headaches.
5. Promoting a normal positioning of the spine and preventing muscle and fascial restrictions helps promote healthy blood flow and capillary flow to the vertebral discs, reduces excessive disc pressures, and reduces impingement pressure and entrapments on nerves, thus decreasing neurogenic or radicular pain and/or parasthesias (numbness or tingling).

In summary, proper posture is vital to a person's overall health, comfort and well-being. A brace in accordance with the invention may be used to help promote proper posture.

It will be appreciated that numerous variations and uses of the invention are possible, within the scope of the claims.

What is claimed is:

1. A method of encouraging proper posture during a golf swing, comprising the steps of:
   providing a brace consisting of a single continuous strap and a buckle;
   placing the brace on a golfer, with a first diagonal strap portion and a second diagonal strap portion crossing each other across the golfer's back;
   providing resistance to excessive bending of the golfer's back during a golf swing by adjusting the brace to provide tension prior to the golf swing and by leaving the tensioned brace in position during the golf swing; and
   removing the brace from the golfer after the golfing activity is completed.

2. The method of claim 1 further comprising the step of:
   providing a garment comprising an inner lining, an outer shell, and at least one tunnel or loop; and
   passing the brace through at least tunnel or loop of the garment.

3. The method of claim 2 wherein at least one tunnel or loop of the garment is padded.

4. The method of claim 2 wherein at least one tunnel or loop of the garment is integral with the inner lining.

5. The method of claim 2 wherein the outer shell comprises at least one opening for providing access to the area between the inner lining and the outer shell for access to the brace.

6. The method of claim 1 wherein the brace further comprises a first front strap portion and a second front strap portion, wherein the buckle adjustably connects the first front strap portion and the second front strap portion.

7. A method of encouraging proper posture during a golf swing, comprising the steps of:
   (a) providing an adjustable brace comprising a first diagonal strap portion and a second diagonal strap portion;
   (b) placing the adjustable brace on a golfer, with the first diagonal strap portion extending along the golfer's back from one shoulder downwardly and diagonally and with the second diagonal strap portion extending along the golfer's back from the other shoulder downwardly and diagonally, with the brace in position during the golf swing such that the brace provides resistance to excessive bending of the golfer's back during the golf swing; and
   (c) removing the adjustable brace from the golfer after the golfing activity is completed.

8. The method of claim 7 wherein the brace comprises a single continuous strap having a first end and a second end and means for joining the first end a second end.

9. The method of claim 8 wherein the means for joining the first end and second end comprises a buckle.

10. The method of claim 7 further comprising the step of:
    providing a garment comprising at least one tunnel or loop; and
    passing the brace through at least tunnel or loop of the garment.

11. The method of claim 10 wherein the garment comprises an outer shell and an inner lining and at least one tunnel or loop of the garment is integral with the inner lining.

12. The method of claim 11 wherein the outer shell comprises at least one opening for providing access to the area between the inner lining and the outer shell for access to the brace.

13. A method of encouraging proper posture during a golf swing, comprising the steps of:
    (a) providing a brace comprising a plurality of strap portions;
    (b) securing the brace to a garment;
    (c) placing the garment and brace on a golfer, with the brace in position during the golf swing such that the brace provides resistance to excessive bending of the golfer's back during the golf swing; and
    (d) removing the garment and brace from the golfer after the golfing activity is completed;

wherein the garment comprises at least one tunnel or loop and the step of securing the brace to the garment comprises passing the brace through at least one tunnel or loop of the garment.

14. The method of claim 13 wherein the garment comprises an outer shell and an inner lining and at least one tunnel or loop of the garment is integral with the inner lining.

15. The method of claim 14 wherein the outer shell comprises at least one opening for providing access to the area between the inner lining and the outer shell for access to the brace.

16. The method of claim 13 wherein the brace is adjustable.

* * * * *